United States Patent

Furusawa et al.

[11] Patent Number: 5,840,017
[45] Date of Patent: Nov. 24, 1998

[54] ENDOSCOPE SYSTEM

[75] Inventors: Koichi Furusawa; Rensuke Adachi, both of Tokyo, Japan

[73] Assignee: Asahi Kogaku Kogyo Kabushiki Kaisha, Tokyo, Japan

[21] Appl. No.: 691,911

[22] Filed: Aug. 1, 1996

[30] Foreign Application Priority Data

Aug. 3, 1995 [JP] Japan ................................ 7-198287

[51] Int. Cl.⁶ ...................................................... A61B 1/06
[52] U.S. Cl. .......................... 600/160; 600/109; 600/178
[58] Field of Search ................................ 600/109, 160, 600/178, 181, 182, 476, 478

[56] References Cited

U.S. PATENT DOCUMENTS

| | | | |
|---|---|---|---|
| 4,273,110 | 6/1981 | Groux | 600/178 |
| 4,646,724 | 3/1987 | Sato et al. | 600/178 |
| 4,653,478 | 3/1987 | Nagasaki et al. | 600/178 |
| 4,782,819 | 11/1988 | Adair | 600/178 |
| 4,821,117 | 4/1989 | Sekigiguchi | 600/160 |
| 4,974,076 | 11/1990 | Nakamura et al. | 600/109 |
| 5,105,269 | 4/1992 | Nakamura et al. | 600/109 |
| 5,220,912 | 6/1993 | Nakasima et al. | 600/178 |
| 5,590,660 | 1/1997 | MacCaulay et al. | 600/160 |
| 5,667,474 | 9/1997 | Nishimura | 600/160 |
| 5,701,903 | 6/1995 | Sano et al. | 600/160 |
| 5,749,830 | 10/1994 | Kanelo et al. | 600/160 |

*Primary Examiner*—Gene Mancene
*Assistant Examiner*—Ira Hatton
*Attorney, Agent, or Firm*—Greenblum & Bernstein, P.L.C.

[57] ABSTRACT

An endoscope system for examining organic tissue that uses a light source to generate persistent fluorescence (that is, fluorescence that remains after the generating source is turned off or removed) in organic tissue. Two shutter mechanisms are controlled such that only the persistent fluorescence is allowed to reach an image receiving device, such as a CCD area sensor. The two shutters are controlled such that the CCD area sensor is exposed to the persistent fluorescence either once or a plurality of times before the image data is output. If the CCD is only exposed once, a number of CCD outputs are accumulated in a picture memory. The image generated from either the CCD output (for the plurality of exposures case) or the picture memory (for the single exposure case) is displayed on a display device.

8 Claims, 9 Drawing Sheets

ENDOSCOPE SYSTEM

BACKGROUND OF THE INVENTION

The present invention relates to an endoscope system for observing organic tissue, specifically for observing organic tissues displaying fluorescence when appropriately illuminated. More particularly, the present invention relates to an endoscope for recording moving pictures during observation of fluorescence.

One type of endoscope capable of recording fluorescing tissue is known as the Laser Induced Fluorescence system (LIF system). In the LIF system, a laser, typically an He-Cd laser, emits coherent ultraviolet or visible radiation having a relatively short wavelength in a range that excites tissue in a known manner. The laser radiation is used to illuminate and excite organic tissue, typically a wall of a body cavity, and the illuminated cells fluoresce. The excited cells generate fluorescence having a longer wavelength (in the visible region) than the illumination (laser) light.

In general, cancerous cells generate relatively weak fluorescence in comparison to normal cells. Accordingly, the amount of fluorescence can be used to distinguish cancerous cells from normal cells. In the LIF system, an image detector is therefore provided with a filter that allows the transmission of only the wavelength range of the fluorescence. The filter blocks the transmission of illumination light. Accordingly, only the fluorescence of the tissue is detected.

A disadvantage of the LIF system is the expense: the cost of an LIF system is high because lasers (such as the He-Cd laser) having the appropriate wavelength for excitation are expensive. Furthermore, the filter at the image detector reduces the amount of available light.

Other known endoscopes use a broad-spectrum light source instead of a coherent laser source. A first filter is arranged between the broad-spectrum light source and the tissue, and limits the wavelength range of the illuminating radiation to the excitation wavelength, usually in the near ultraviolet range. A second filter is arranged before the detector to allow only the transmission of light within the range of wavelengths of fluorescing tissue. Unfortunately, the use of the two filters decreases the intensity of the received light.

SUMMARY OF THE INVENTION

It is therefore an object of the present invention to provide an improved endoscope capable of observing fluorescing organic tissue, and recording moving pictures, without decreasing the amount of available light. It is a further object of the invention to limit the recorded light to that emitted by fluorescing tissue while avoiding the use of filters for illumination light or received light.

The present invention is directed to an endoscope that satisfies this need.

According to an aspect of the present invention, an endoscope system for examining organic tissue includes a light source, an image receiving device, an endoscope, first and second shutter means, and a control circuit.

The light source emits both visible light and other excitation radiation that generates persistent fluorescence in the organic tissue.

The image receiving device detects the persistent fluorescence and outputs images formed from the persistent fluorescence.

The endoscope guides the excitation radiation to the organic tissue and also guides the persistent fluorescence to the image receiving device.

The first shutter means controls transmission of the excitation radiation from the light source to the organic tissue and the second shutter means controls transmission of the persistent fluorescence from the organic tissue to the image receiving device.

The control circuit controls the first shutter means and the second shutter means. In particular, the control circuit controls the second shutter means to start transmitting the persistent fluorescence to the image receiving device immediately after the first shutter means stops transmitting the excitation radiation to the organic tissue.

More particularly, the image receiving device includes a CCD area sensor and a CCD driver. The CCD area sensor generates a voltage when it receives visible light or other excitation radiation. Further, the CCD area sensor outputs image data in response to a transfer gate pulse generated and sent by the CCD driver. The CCD driver generates the transfer gate pulse at a predetermined interval. Thus, the CCD area sensor outputs image data at the same predetermined interval.

In a particular case, the image receiving device also includes an image processor that processes image data output by the CCD area sensor.

In this particular case, the control circuit controls the first and second shutter means a plurality of times during the predetermined interval. Thus, the CCD area sensor is exposed to the persistent fluorescence a plurality of times. The CCD area sensor accumulates voltage generated by each exposure to the persistent fluorescence and the cumulative voltage forms the image data that is output in response to the transfer gate pulse. The image processor then outputs the image data received from the CCD area sensor.

In a further particular case, the image processor includes a picture memory that receives the output of the CCD area sensor. In this further particular case, the control circuit controls the first and second shutter means once during the predetermined interval. Thus, the CCD area sensor is exposed to the persistent fluorescence once before outputting image data The picture memory receives image data of the persistent fluorescence over a plurality of transfer gate pulses and accumulates intensity values. The image processor then outputs the image formed by the cumulative intensity value in the picture memory.

Preferably, the first shutter means includes a first shutter located between the light source and the organic tissue, and the second shutter means includes a second shutter located between the organic tissue and the image receiving device.

In a particular case, the second shutter means may include an electronic shutter portion of the CCD area sensor that is controlled by the CCD driver.

DETAILED DESCRIPTION OF THE PREFERRED EMBODIMENTS

Figure 1:
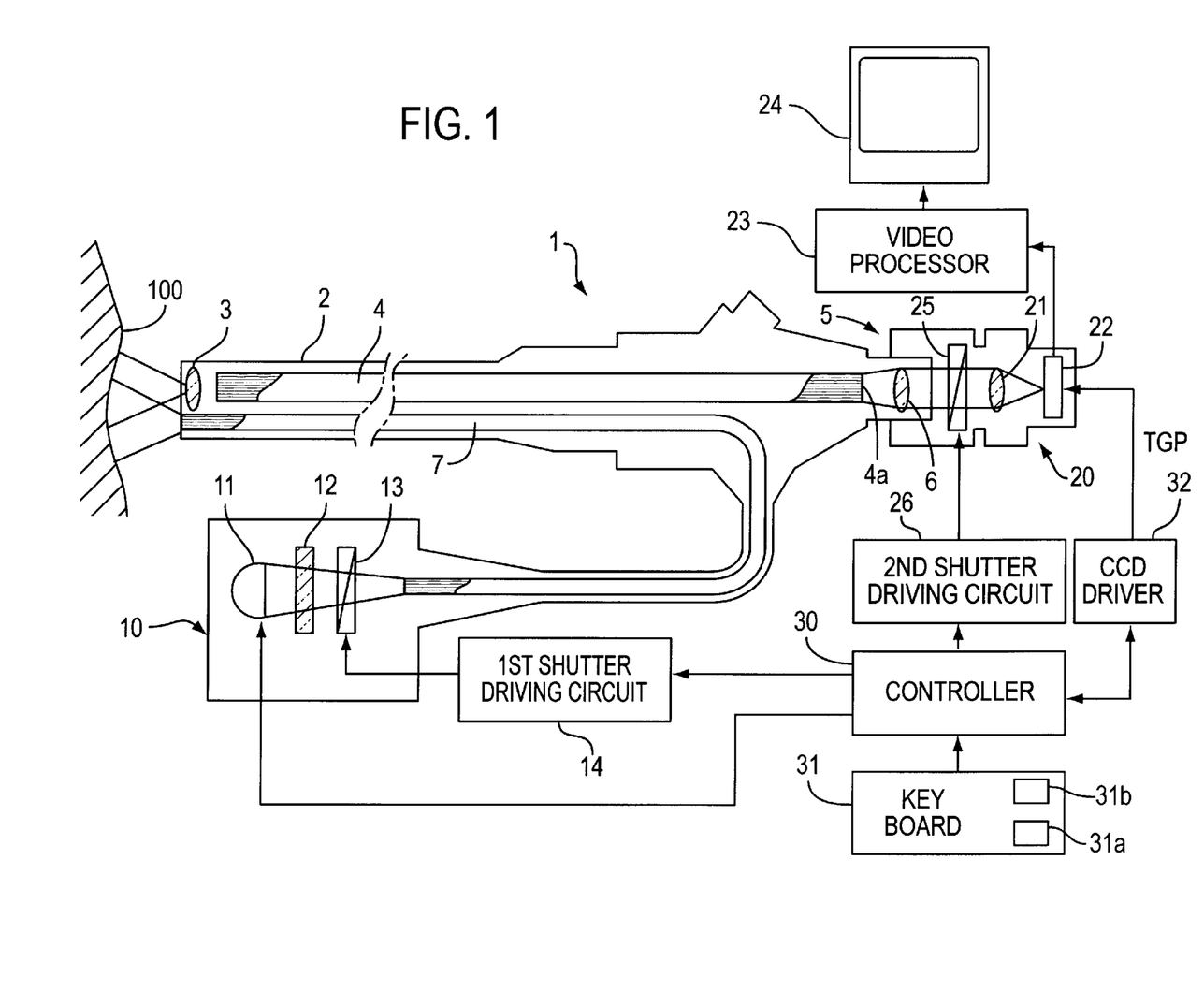
FIG. 1 shows a schematic of a fluorescence-recording endoscope system according to a first embodiment of the present invention.

FIG. 1 shows the general construction of an endoscope system according to the first embodiment of the present invention.

The endoscope system of the first embodiment includes an endoscope 1 having an insertion unit 2, an observing unit 5, a light source device 10, a color video camera 20 attached to the observing unit 5, and various control circuits (described later). An image guide fiber bundle 4 and a light guide fiber bundle 7 are arranged in the insertion unit 2.

Organic tissue 100, such as the wall of a body cavity, is illuminated by light emitted from a light source 11 of the light source device 10 and transmitted through the light guide fiber bundle 7. The light source 11 emits "white" light, including an ultraviolet radiation component (as excitation radiation) having a wavelength range of 300 nm through 500 nm. The organic tissue 100 fluoresces (i.e., generates fluorescence) in a wavelength range of 500 nm through 600 nm in response to the excitation radiation.

The light source device 10 is further provided with infrared cut filter 12 and a first shutter 13. The first shutter 13 is a known high-speed shutter device (one such device would be an electro-optical Kerr cell shutter or the like) that constitutes a first switching device for turning ON and OFF the illumination from the light source 11, i.e., for interrupting the transmission of light between the light source 11 and the organic tissue 100. The first shutter 13 is located between the infrared cut filter 12 and the incident end surface of the light guide fiber bundle 7.

An image of the organic tissue 100 is formed by an objective lens 3 within the distal end of the insertion unit 2. The image of the organic tissue 100 is transferred by the image guide fiber bundle 4 to the observing unit 5.

The transferred image of the organic tissue 100 exits an exit end 4a of the image guide fiber bundle 4, passes through an eyepiece lens 6, a second shutter 25, and a taking lens 21, and forms the image on a CCD area sensor 22. The CCD area sensor 22 is driven by a CCD driver 32 and can sense the entire wavelength range of visible radiation (light). The CCD area sensor 22 forms a portion of a detecting device that detects light from the organic tissue 100 and outputs image data describing the organic tissue 100. The output image data from the CCD area sensor 22 is input into a video processor 23 that processes the image data and displays a moving picture of the image on a monitor 24. The video processor 23 includes at least an amplifier to amplify the CCD signals and an A/D converter to convert the amplified signals to n-bit image data.

The second shutter 25 is disposed between the eyepiece lens 6 and the taking lens 21. The second shutter 25 is a high-speed shutter similar to the first shutter 13, and acts as a second switching device for turning image detection (by the CCD area sensor 22) ON and OFF.

A controller 30 controls the first and second shutters 13 and 25 via a first shutter driving circuit 14 and a second shutter driving circuit 26, respectively. The controller 30 further controls the light source 11 (to turn ON and OFF) and a CCD driver 32. The CCD driver 32 generates a transfer gate pulse (TG pulse) and sends it to the CCD area sensor 22, controlling the (predetermined) timing at which image data from the CCD area sensor 22 is output. A keyboard 31 is connected with the controller 30 to allow the input of instructions by an operator. The keyboard 31 is provided with a main switch 31a and a fluorescence recording switch 31b. A control circuit includes the controller 30 and the keyboard 31.

The control circuit has a fluorescence recording mode and a normal recording mode. The fluorescence recording mode is selected when the fluorescence recording switch 31b is turned ON, and the normal recording mode is selected when the fluorescence recording switch 31b is OFF. In the context of this specification, for the first or second shutters 13 or 25, an open shutter corresponds to "turning ON" illumination by the light source 11 or detection by the CCD 22, respectively, while a closed shutter corresponds to "turning OFF" illumination or detection, respectively.

In the fluorescence recording mode, the first shutter 13 is controlled so that the illumination by the light source 11 alternates between turning ON and OFF in a predetermined cycle That is, the first shutter 13 alternates between open and closed, and the organic tissue 100 is thereby illuminated intermittently by the light source 11. The cycle of opening/closing operation is, for example, 5 ms to 20 ms. The second shutter 25 is also controlled so that the light from the organic tissue 100 is incident to the CCD area sensor 22 only when the illumination is turned OFF. The second shutter opens immediately after the illumination is turned OFF, and closes before the first shutter 13 opens.

Since the illumination includes excitation light (i.e., radiation within the excitation wavelength range) the illuminated organic tissue 100 generates fluorescence. Since fluorescence from cancerous cells is weaker than that from normal cells, cancerous cells are distinguishable by fluorescent observation. The intensity of fluorescence is much lower than reflected illumination light. However, since the fluorescence persists 5 ns through 10 ns after the excitation light is removed, the CCD area sensor 22 detects fluorescence only after the illumination turns OFF. Furthermore, since one iteration of a detected image is too weak to display, the embodiment accumulates a plurality of detected images into a single cumulative image, and sends the cumulative image to the monitor 24.

The driver 32 generates a TG pulse such that the CCD receives an image of fluorescing tissue a plurality of times. The video processor 23 displays the integrated (cumulative) image received by the CCD area sensor 22 on the monitor 24.

Conversely, in the normal recording mode, the first and second shutters 13 and 25 open during the image recording operation, allowing ordinary exposures to be taken.

Figure 2:
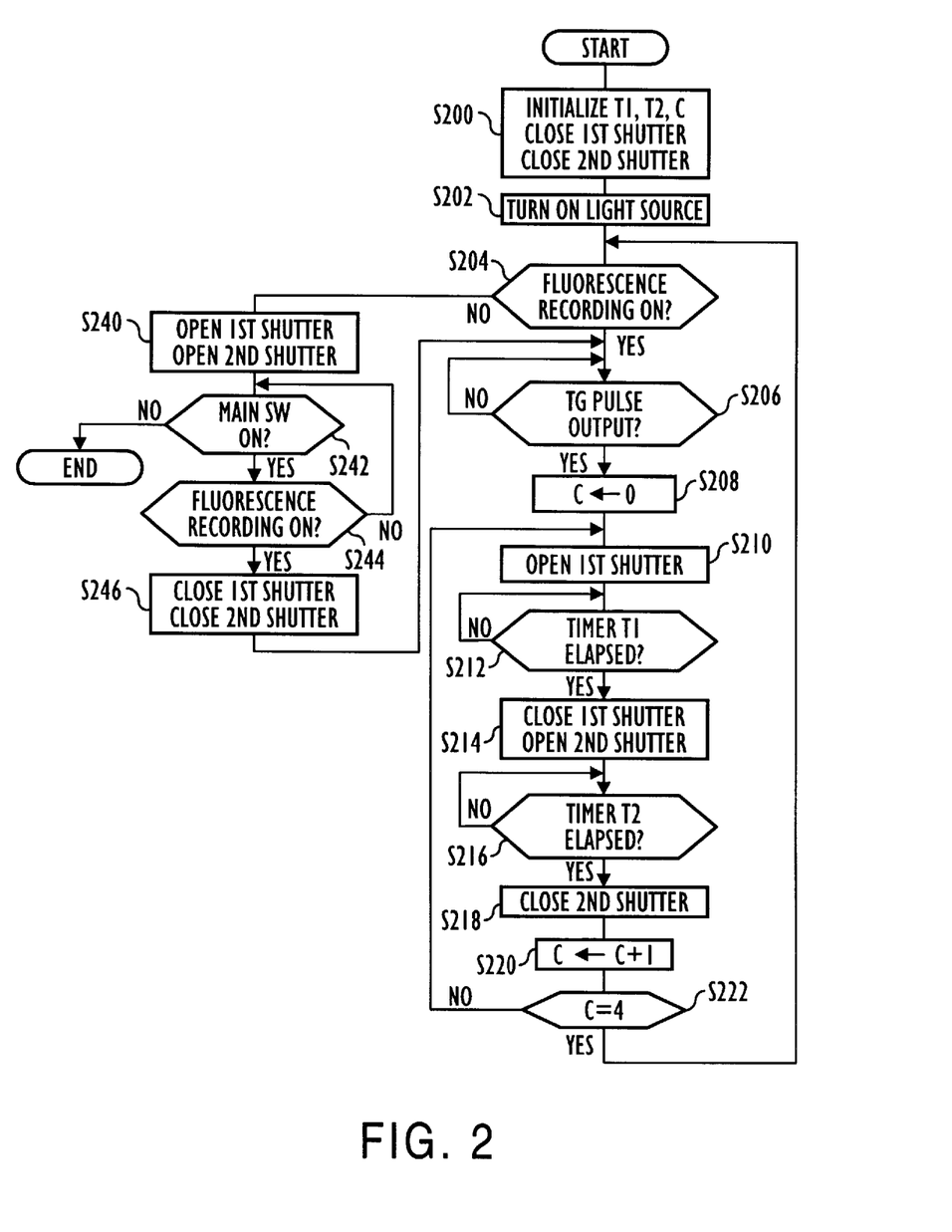
FIG. 2 is a flow chart showing a recording process of the first embodiment.

FIG. 2 is a flow chart of the operation of the endoscope system according to the first embodiment. When the endoscope system of the first embodiment is first activated, in step S200, the controller 30 initializes (i.e., resets or sets to predetermined values) at least a counter C, a first timer T1 and a second timer T2 (described later), and closes (if open) the first shutter 13 and the second shutter 25. Next, in step S202, the controller 30 turns ON the light source 11. In step S204, the controller 30 checks if the fluorescence recording switch 31b is ON or OFF. If the fluorescence recording switch 31b is OFF, control proceeds to step S240 for normal recording (described later).

If the fluorescence recording switch is ON (YES at step S204), the controller 30 loops in step S206 until the TG pulse is output, signifying that the CCD driver 32 has completed transferring CCD image data to the video processor 23. After the TG pulse is output, the counter C is reset to 0 in step S208. The counter C is used to count iterations of integration of CCD data per TG pulse; that is, counter C is used to count the number of times the CCD area sensor 22 is exposed to the fluorescence per TG pulse.

In step S210, the first shutter 13 is opened and is left open for a first predetermined time. The first predetermined time is sufficiently long to induce persistent fluorescence in organic tissues when illuminated by the excitation radiation emitted by the light source 11. The first predetermined time is stored in the first timer T1 at step S200, and is counted down by the controller 30 in step S212 When the first timer T1 elapses (YES at step S212), the first shutter 13 is closed, and the second shutter 25 is controlled to open when the first shutter 13 closes at step S214. The second shutter 25 is left open for a second predetermined time, the second predetermined time being at least as long as the duration of persistent fluorescence. The second predetermined time is stored in a second timer T2 in step S200, and is counted down by the controller 30 at step S216. When the second timer T2 elapses (YES at step S216), the second shutter 25 is closed at step S218 and counter C is incremented at step S220. The controller checks the counter C at step S222. If the counter is equal to the target number of iterations of integration of CCD voltage per TG pulse, (in this case 4 iterations, YES at step S222), the controller goes to step 204 and the image data in the CCD area sensor 22 is sent to the video processor 23 in response to the next TG pulse emitted by the CCD driver 32. If the counter is not equal to the specified number (in this case, not equal to 4 at step S222), the controller 30 returns to step S210 to accumulate subsequent image data.

As previously noted, at step S204, if the fluorescence recording switch 31b is OFF (NO at step S204), normal recording is performed starting at step S240. In the normal go recording process, the controller 30 opens both the first shutter 13 and the second shutter 25 at step S240. The controller 30 then checks the main switch 31a at step S242. At step S242, if the main switch is OFF (NO at step S242), the recording process is ended, i.e., the endoscope system turns OFF.

If the main switch 31a is ON (YES at step S242), the controller 30 checks if the fluorescence recording switch 31b is ON at step S244. If the fluorescence recording switch 31b is OFF (NO at step S244), the controller 30 returns to step S242. If the fluorescence recording switch 31b is ON (YES at step S244) the controller 30 closes the first shutter 13 and the second shutter 25 and proceeds to step S206.

FIGS. 3A through 3E show approximate timing charts for the fluorescence recording mode according to the first embodiment. The timing line in each of FIGS. 3A through 3E is broken in the span of a single TG pulse period to signify that many iterations (in the example of FIG. 2, only 4 iterations) of voltage accumulation may be taken within each TG pulse period. The timing charts show generation of the TG pulses, the operation of the first shutter 13 and the second shutter 25, an approximation of the light intensity of the fluorescence detected by the CCD area sensor 22, and the integrated (accumulated) image data of the CCD area sensor 22. The approximate light intensity and accumulated image data are representative of both a single picture element of the CCD area sensor 22 and the average of all picture element.

Figure 3A:
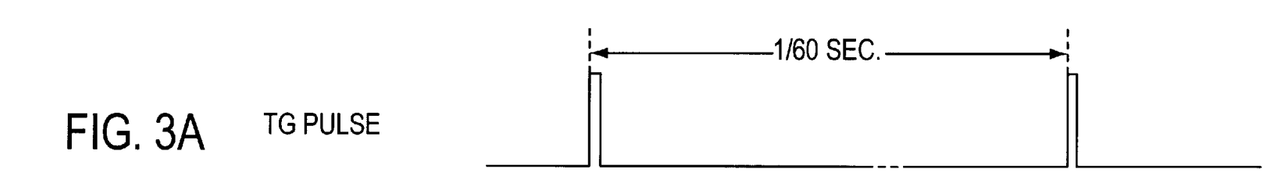
FIGS. 3A through 3E are timing charts showing a fluorescence-recording process of the first embodiment.
Figure 3B:
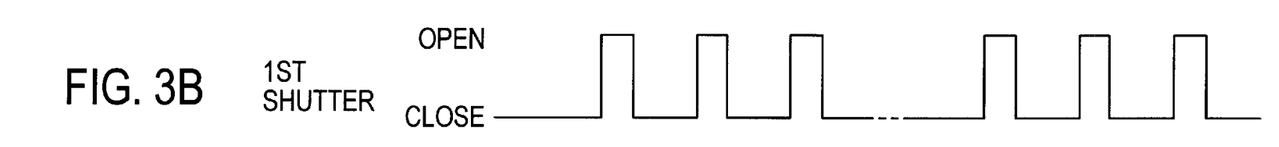
Figure 3C:
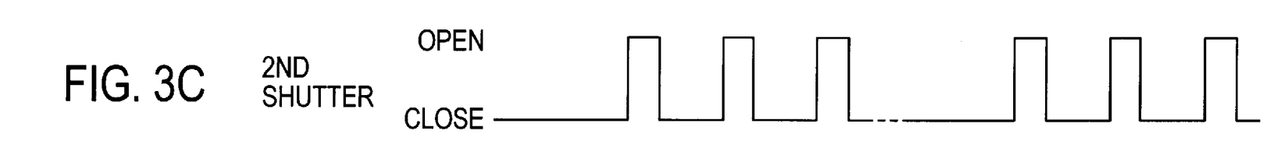
Figure 3D:
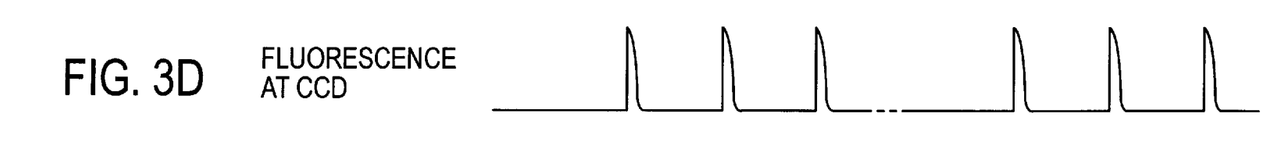
Figure 3E:
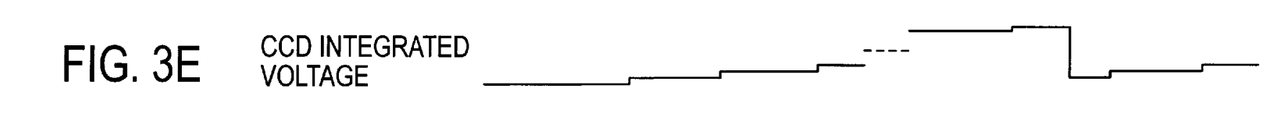

As shown in FIG. 3A, a TG pulse is generated every 1/60th of a second. In the interval between TG pulses, the first shutter 13 opens and closes a predetermined number of times. In the example shown in FIG. 3A, the first shutter 13 and second shutter 25 open and close 4 times between sequential TG pulses. As previously described, the second shutter 25 follows the first shutter 13, opening the same number of times. As shown in FIG. 3E, the accumulated (integrated) voltage of the CCD area sensor 22 increases and is output according to the leading edge of the TG pulses.

Figure 4:
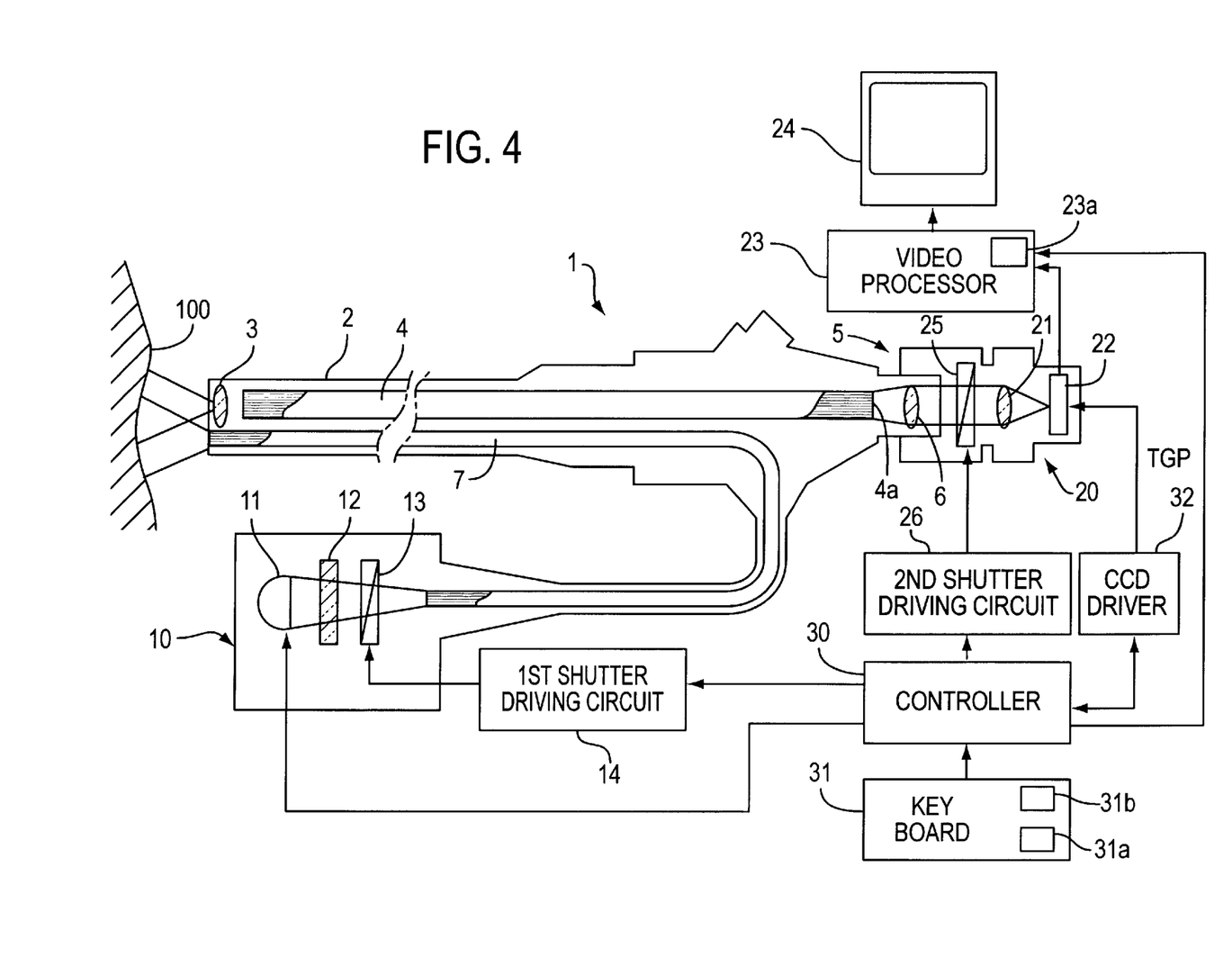
FIG. 4 shows a schematic of a fluorescence-recording endoscope system according to a second embodiment of the present invention.

FIG. 4 shows the general construction of an endoscope system according to the second embodiment of the present invention. In the second embodiment, portions shown but not described, and having reference numbers identical to the first embodiment, have the same description and function.

The second embodiment is different from the first embodiment in that the video processor 23 is provided with a picture memory 23a to store image data output from the CCD area sensor 22, and the picture memory 23a is used to accumulate a number of images of persistent fluorescence into a single, brighter image (instead of integrating voltage in the CCD itself, as in the first embodiment). The CCD area sensor 22 is driven by the CCD driver to output image data to the picture memory 23a a plurality of times (4 times in this example) every 1/60th of a second, i.e., once every 1/240th of a second. The intensity values of accumulated image data corresponding to the cumulative image of persistent fluorescence stored in the picture memory 23a is increased with each iteration, and the stored image is displayed on the monitor 24 every 1/60th of a second.

Figure 5:
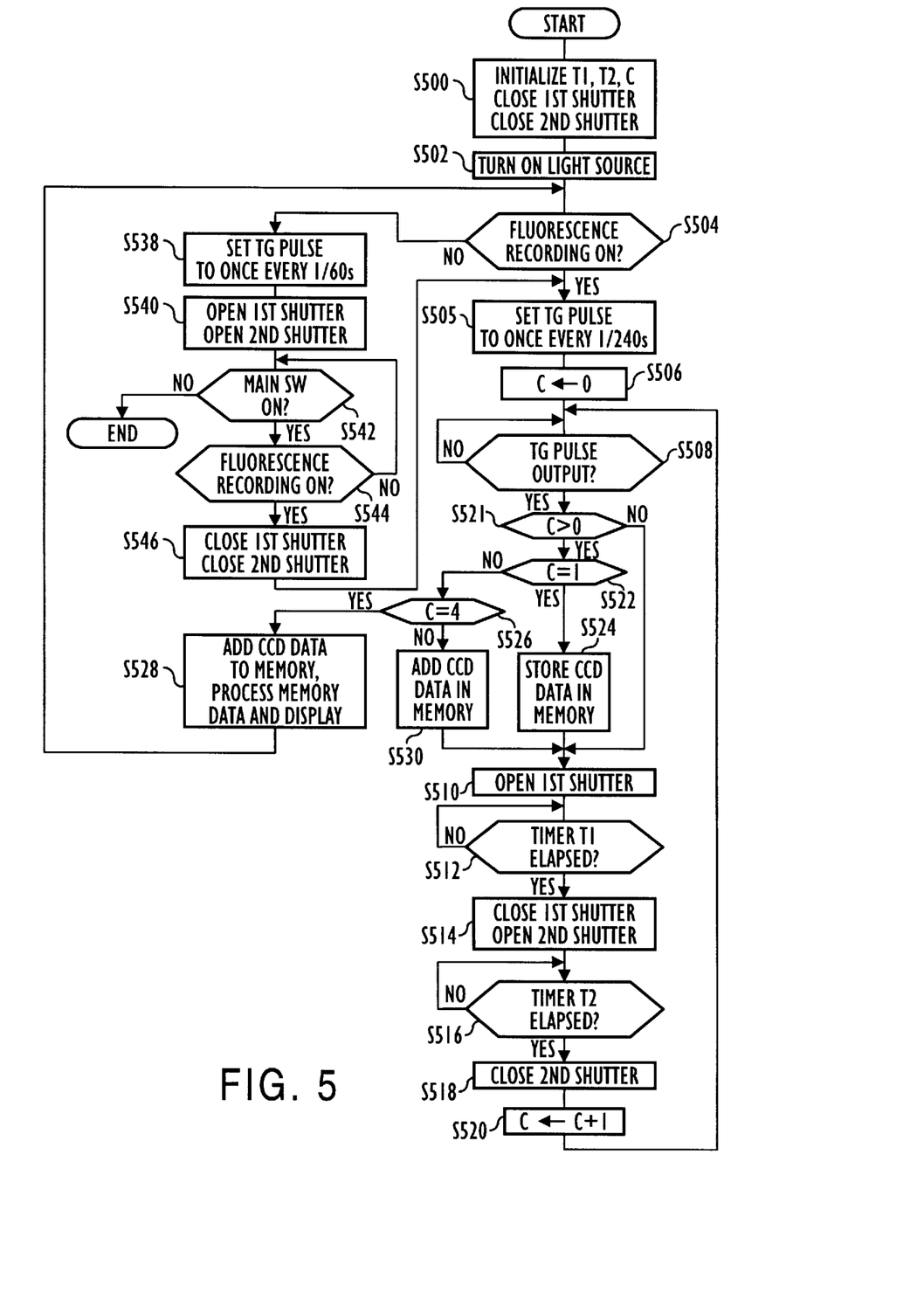
FIG. 5 is a flow chart showing a recording process of the second embodiment.

FIG. 5 is a flow chart of the operation of the endoscope system according to the second embodiment. When the endoscope system of the second embodiment is first activated, in step S500, the controller 30 initializes (i.e., resets or sets to predetermined values) at least a counter C, a first timer T1 and a second timer T2 (described later), and closes (if open) the first shutter 13 and the second shutter 25. Next, in step S502, the controller 30 turns on the light source 11. In step S504, the controller 30 checks if the fluorescence recording switch 31b is ON or OFF. If the fluorescence recording switch 31b is OFF, control proceeds to step S538 for normal recording (described later).

If the fluorescence recording switch is ON (YES at step S504), the TG pulse is set to be output once every 1/240 second in step S505 (so that the CCD area sensor 22 will output image data 4 times within 1/60 second, as explained above). Counter C is reset to 0 in step S506 and then the controller 30 loops in step S508 until the TG pulse is output, signifying that the CCD driver 32 has completed transferring CCD image data to the video processor 23. Counter C is used to count iterations of accumulation of image data in the picture memory 23a.

The controller checks the counter C at step S521 If the counter C is not greater than 0 (NO at step S521), the controller 30 goes to step S510 because the first iteration has not been completed yet. If the counter C is greater than 0 (YES at step S521), the controller 30 then checks the counter C again at step S522.

If the counter C is equal to 1 (Y at step S522), signifying that the available CCD data is the first iteration, the image data in the CCD area sensor 22 is stored in the picture memory 23a at step S524. The process then goes to step S510 to accumulate subsequent image data. If the counter C is not equal to 1 (N at step S522), control proceeds to step S526.

At step S526, the controller 30 checks if the counter C is equal to the target number of iterations (in this case, 4 iterations) of accumulation of image data in the picture memory 23a. If the target number of iterations of accumulation of image data in the picture memory 23a has not been reached, (in this case 4 iterations, NO at step S526), the image data in the CCD area sensor 22 is processed and added to that stored in the picture memory 23a, whereupon the process goes to step S510 to accumulate subsequent image data.

If the target number of iterations of accumulation of image data in the picture memory 23a has been reached, (in this case 4 iterations, YES at step S526), the image data in the CCD area sensor 22 is processed, added to that stored in the picture memory 23a and the cumulative image in the picture memory 23a is displayed on the monitor 24 in step S528. The controller 30 then proceeds to step S504.

In step S510, the first shutter 13 is opened and is left open for a first predetermined time. The first predetermined time is sufficiently long to induce persistent fluorescence in organic tissues when illuminated by the excitation radiation emitted by the light source 11. The first predetermined time is stored in the first timer T1 at step S500, and is counted down by the controller 30 in step S512. When the first timer T1 elapses (YES at step S512), the first shutter 13 is closed, and the second shutter 25 is controlled to open when the first shutter 13 closes at step S514. The second shutter 25 is left open for a second predetermined time, the second predetermined time being at least as long as the duration of persistent fluorescence. The second predetermined time is stored in a second timer T2 in step S500, and is counted down by the controller 30 at step S516. When the second timer T2 elapses (YES at step S512), the second shutter 25 is closed at step S518 and the counter C is incremented at step S520. Control then returns to step S508 for the next iteration.

As previously noted, at step S504, if the fluorescence recording switch 31b is OFF (NO at step S504), normal recording is performed starting at step S538. In the normal recording process, the controller 30 sets the TG pulse to be output once every 1/60 s in step S538 (so that the CCD area sensor 22 will output image data every 1/60 second, as explained above). The controller opens both the first shutter 13 and the second shutter 25 at step S540 and then checks the main switch 31a at step S542. At step S542, if the main switch is OFF (NO at step S542), the recording process is ended, i.e., the endoscope system turns OFF.

If the main switch 31a is ON (YES at step S542), the controller 30 checks if the fluorescence recording switch 31b is ON at step S544. If the fluorescence recording switch 31b is OFF (NO at step S544), the controller 30 returns to step S542. If the fluorescence recording switch 31b is ON (YES at step S544) the controller 30 closes the first shutter 13 and the second shutter 25 and proceeds to step S505.

FIGS. 6A through 6F show approximate timing charts for the fluorescence recording mode for the second embodiment. The arrow denoting a 1/60th second interval for FIGS. 6A through 6E is broken to signify that many iterations (in the example of FIG. 5, only 4 iterations) of image data intensity accumulation may be taken within each 1/60th of a second, each iteration corresponding to a TG pulse. The timing charts show generation of the TG pulses, the operation of the first shutter 13 and the second shutter 25, an approximation of the light intensity of the fluorescence detected by the CCD area sensor 22, the integrated (accumulated) voltage of the CCD area sensor 22, and the intensity of the image data stored in the picture memory 23a. The approximated light intensity and accumulated image data are representative of both a pixel of the CCD area sensor 22 and the average of all pixels.

Figure 6A:
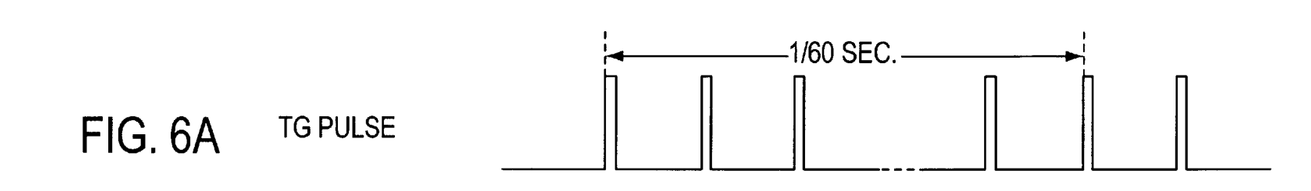
FIGS. 6A through 6F are timing charts showing a fluorescence-recording process of the second embodiment.
Figure 6B:
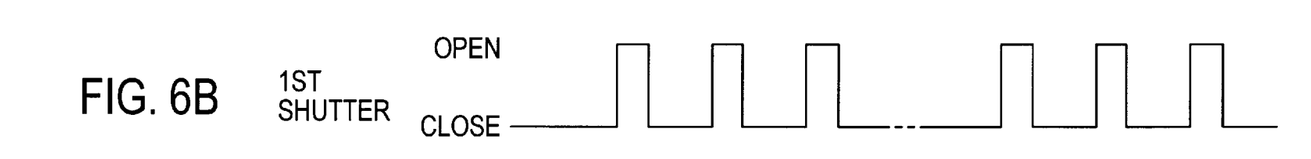
Figure 6C:
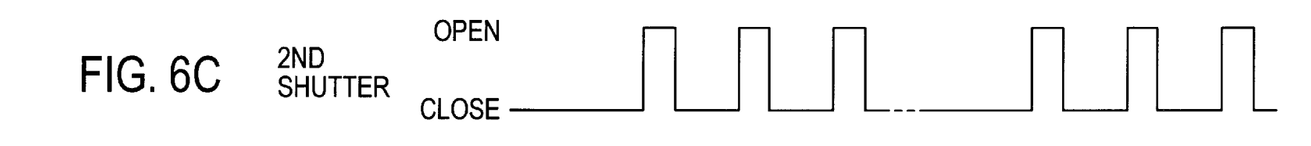
Figure 6D:
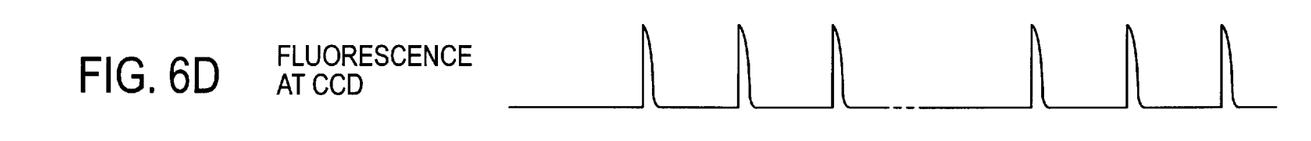
Figure 6E:
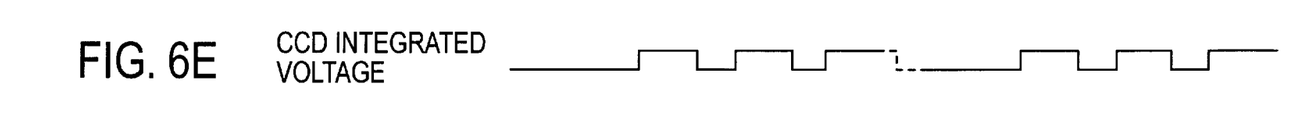
Figure 6F:
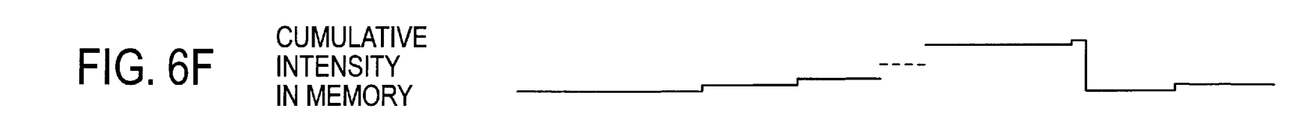

As shown in FIG. 6A, a TG pulse is generated a predetermined number of times every 1/60th of a second, for example, 4 times (giving a TG pulse period of 1/240th of a second). In the interval between TG pulses, the first shutter 13 opens and closes. The second shutter 25 follows the first shutter 13. As shown in FIG. 6E, the integrated voltage in the CCD area sensor 22 is output according to the leading edge of the TG pulse. As shown in FIG. 6F, data in the picture memory 23a representative of intensity increases and is output every 1/60th of a second.

Figure 7:
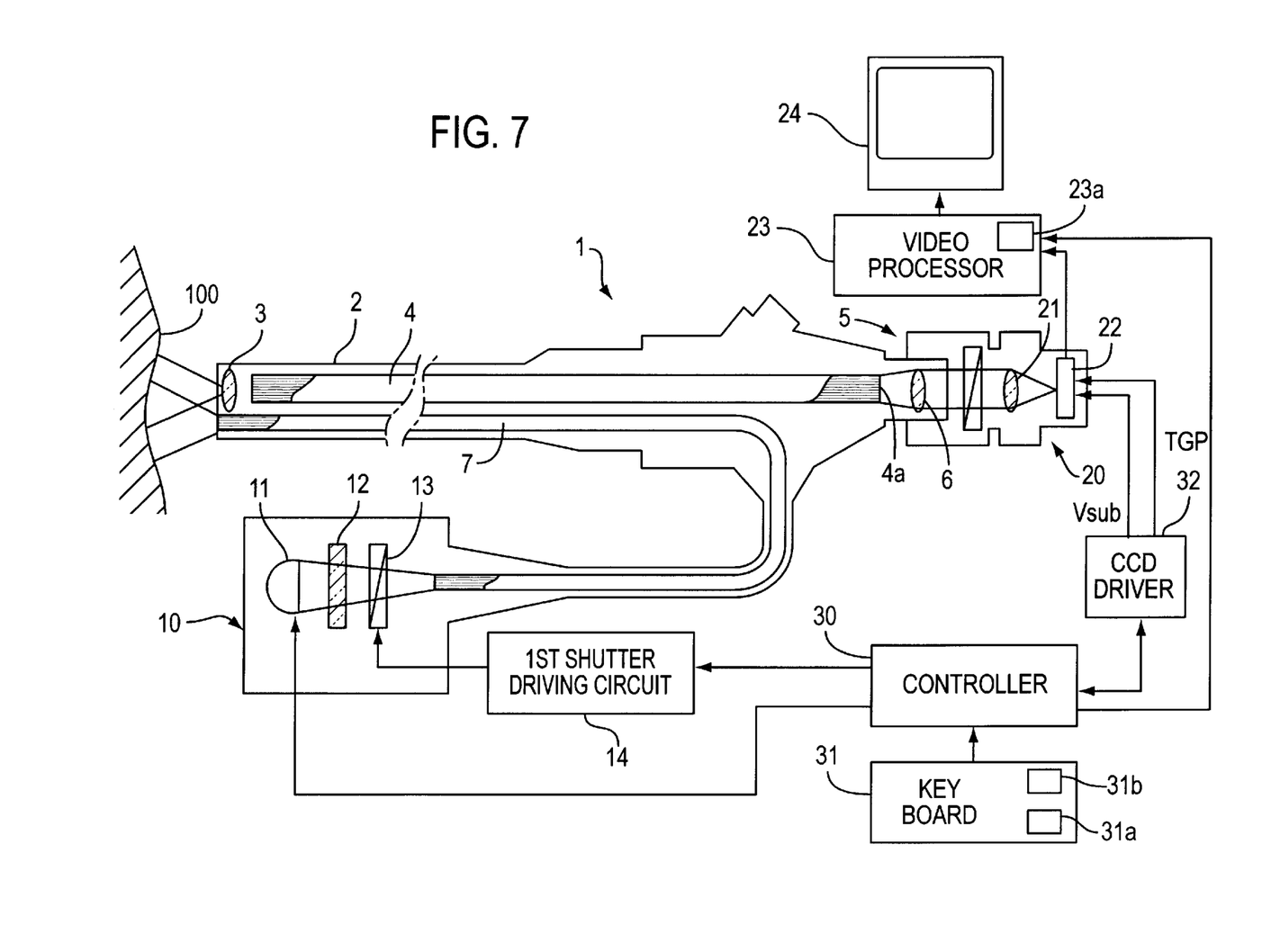
FIG. 7 shows a schematic of a fluorescence-recording endoscope system according to a third embodiment of the present invention.

FIG. 7 shows the general construction of an endoscope system according to the third embodiment of the present invention. In the third embodiment, portions shown but not described, and having reference numbers identical to the second embodiment, have the same description and function.

The third embodiment is different from the second embodiment in that the second shutter 25 and the second shutter driving circuit 26 are replaced by an electronic shutter function in the CCD area sensor 22. The CCD driver 23 controls the electronic shutter function using a shutter signal Vsub. The electronic shutter function operates such that the CCD area sensor 22 does not collect or output image data when the shutter signal Vsub is HIGH, and collects image data when the shutter signal Vsub is LOW. The shutter signal Vsub is synchronized with the first shutter 13 so that when the first shutter 13 opens, the shutter signal Vsub is already HIGH, and when the first shutter 13 closes, the shutter signal Vsub changes to LOW and the CCD 22 collects image data. The shutter signal Vsub is then returned to HIGH before the first shutter 13 is again opened.

Figure 8:
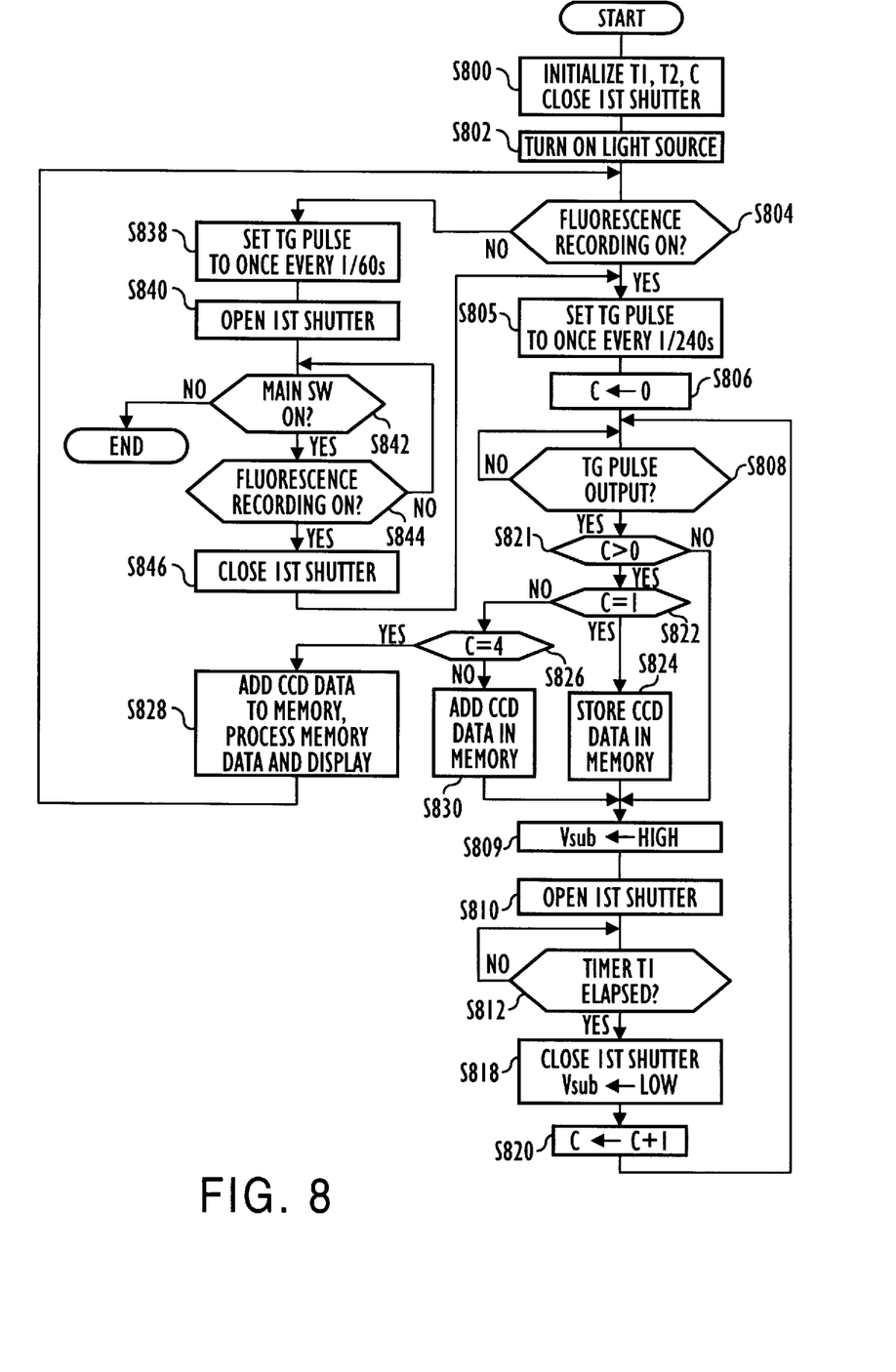
FIG. 8 is a flow chart showing a recording process of the third embodiment.

FIG. 8 is a flow chart of the operation of the endoscope system according to the third embodiment. When the endoscope system of the third embodiment is first activated, in step S800, the controller 30 initializes (i.e., resets or sets to predetermined values) at least a counter C and a first timer T1 (described later), and closes (if open) the first shutter 13. Next, in step S802, the controller 30 turns ON the light source 11. In step S804, the controller 30 checks if the fluorescence recording switch 31b is ON or OFF. If the fluorescence recording switch 31b is OFF, control proceeds to step S838 for normal recording (described later).

If the fluorescence recording switch is ON (YES at step S804), the TG pulse is set to be output once every 1/240 second in step S805 (so that the CCD area sensor 22 will output image data 4 times within 1/60 second, as explained above). Counter C is reset to 0 in step S806 and then the controller 30 loops in step S808 until the TG pulse is output, signifying that the CCD driver 32 has completed transferring CCD image data to the video processor 23. Counter C is used to count iterations of accumulation of image data in the picture memory 23a.

The controller checks the counter C at step S821. If the counter C is not greater than 0 (NO at step S821), the controller 30 goes to step S809 because the first iteration has not been completed yet. If the counter C is greater than 0 (YES at step S821), the controller 30 then checks the counter C again at step S822.

If the counter C is equal to 1 (Y at step S822), signifying that the available CCD data is the first iteration, the image data in the CCD area sensor 22 is stored in the picture memory 23a at step S824. The process then goes to step S809 to accumulate subsequent image data. If the counter C is not equal to 1 (N at step S822), control proceeds to step S826.

At step S826, the controller 30 checks if the counter C is equal to the target number of iterations (in this case, 4 iterations) of accumulation of image data in the picture memory 23a. If the target number of iterations of accumulation of image data in the picture memory 23a has not been reached, (in this case 4 iterations, NO at step S826), the image data in the CCD area sensor 22 is processed and added to that stored in the picture memory 23a, whereupon the process goes to step S809 to accumulate subsequent image data.

If the target number of iterations of accumulation of image data in the picture memory 23a has been reached, (in this case 4 iterations, YES at step S826), the image data in the CCD area sensor 22 is processed, added to that stored in the picture memory 23a and the cumulative image in the picture memory 23a is displayed on the monitor 24 in step S828. The controller 30 then proceeds to step S804.

In step S809, Vsub is set HIGH, disabling the accumulation of image data by the CCD 22. In step S810, the first shutter 13 is opened and is left open for a first predetermined time. The first predetermined time is sufficiently long to induce persistent fluorescence in organic tissues when illuminated by the excitation radiation emitted by the light source 11. The first predetermined time is stored in the first timer T1 at step S800, and is counted down by the controller 30 in step S812. When the first timer T1 elapses (YES at step S812), the first shutter 13 is closed, and the Vsub signal is set to LOW for at least as long as the duration of persistent fluorescence. The counter C is then incremented at step S820. Control then returns to step S808 for the next iteration.

As previously noted, at step S804, if the fluorescence recording switch 31b is OFF (NO at step S804), normal recording is performed starting at step S838. In the normal recording process, the controller 30 sets the TG pulse to be output once every $\frac{1}{60}$ s in step S838 (so that the CCD area sensor 22 will output image data every $\frac{1}{60}$ second, as explained above). The controller opens the first shutter 13 at step S840 and then checks the main switch 31a at step S842. At step S842, if the main switch is OFF (NO at step S842), the recording process is ended, i.e., the endoscope system turns OFF.

If the main switch 31a is ON (YES at step S842), the controller 30 checks if the fluorescence recording switch 31b is ON at step S844. If the fluorescence recording switch 31b is OFF (NO at step S844), the controller 30 returns to step S842. If the fluorescence recording switch 31b is ON (YES at step S844) the controller 30 closes the first shutter 13 and proceeds to step S805.

FIGS. 9A through 9F show approximate timing charts for the fluorescence recording mode for the third embodiment. The timing charts show generation of the TG pulses, the operation of the first shutter 13, the shutter signal Vsub, an approximation of the light intensity of the fluorescence detected by the CCD area sensor 22, the integrated (accumulated) image data of the CCD area sensor 22, and the intensity of the image data stored in the picture memory 23a. The approximate light intensity and accumulated image data are representative of both a pixel of the CCD area sensor 22 and the average of all pixels.

Figure 9A:
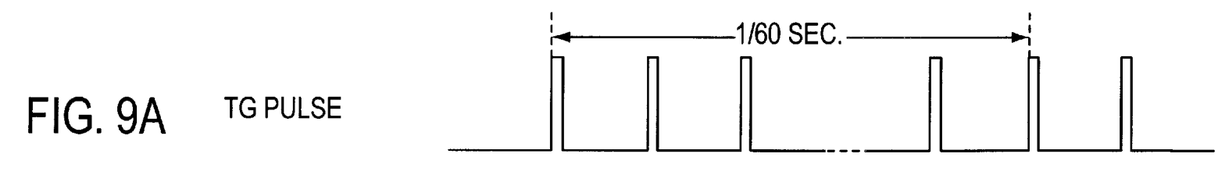
FIGS. 9A through 9F are timing charts showing a fluorescence-recording process of the third embodiment.
Figure 9B:
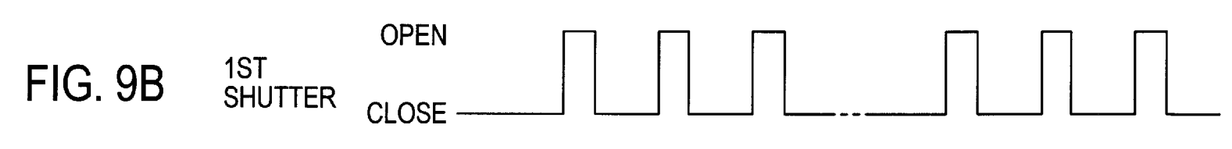
Figure 9C:
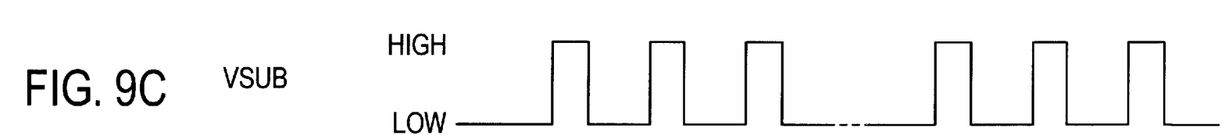
Figure 9D:
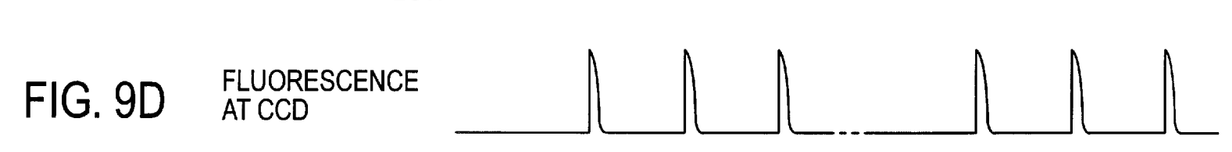
Figure 9E:
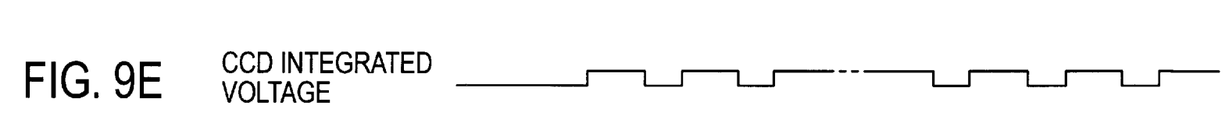
Figure 9F:
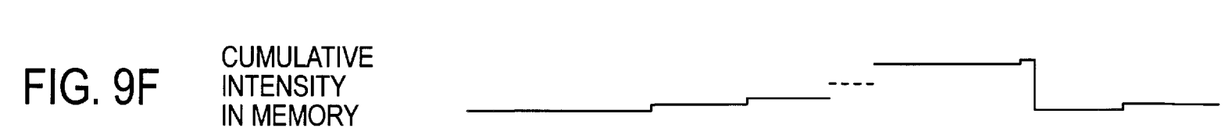

As shown in FIG. 9A, a TG pulse is generated a predetermined number of times every $\frac{1}{60}$th of a second, for example, 4 times (giving a TG pulse period of $\frac{1}{240}$th of a second). In the interval between TG pulses, the first shutter 13 opens and closes. The shutter signal Vsub is set to HIGH with the leading end of the TG pulse, and LOW when the first shutter 13 closes. Accordingly, the shutter signal Vsub is always set to HIGH before the first shutter 13 opens. As shown in FIG. 9E, the integrated voltage in the CCD area sensor 22 is output by the leading edge of the TG pulse. As shown in FIG. 9F, the cumulative image data (representative of the intensity of accumulated persistent fluorescence) in the picture memory 23a increases and is output every $\frac{1}{60}$th of a second.

As described, the embodiments of an endoscope system include a light source for emitting excitation light and generating fluorescence from organic tissue and devices for synchronizing the transmission of excitation radiation to the tissue and the transmission of persistent fluorescence to the CCD such that only the persistent fluorescence is recorded by the CCD. This construction allows the use of a general (broad-spectrum) white light source such as a xenon lamp without using a filter, as the detector detects only the fluorescence when the illumination is removed.

The present disclosure relates to subject matter contained in Japanese patent application No. HEI 7-198287, filed on Aug. 3, 1995, which is expressly incorporated herein by reference in its entirety.

What is claimed is:

1. An endoscope system for examining organic tissue, comprising:

a light source that emits excitation radiation having a component that generates persistent fluorescence in the organic tissue;

an image receiving device that detects said persistent fluorescence and that outputs images formed from said persistent fluorescence;

an endoscope that guides said excitation radiation to the organic tissue and that guides said persistent fluorescence to said image receiving device;

first shutter means for controlling a transmission of said excitation radiation from said light source to the organic tissue;

second shutter means for controlling a transmission of said persistent fluorescence from said organic tissue to said image receiving device;

a control circuit that controls said first shutter means and said second shutter means, said control circuit controlling said second shutter means to start transmitting said persistent fluorescence to said image receiving device immediately after said first shutter means stops transmitting said excitation radiation to the organic tissue.

2. The endoscope device according to claim 1, wherein said image receiving device comprises:

a CCD area sensor that responds to a transfer gate pulse by outputting image data; and a CCD driver that generates said transfer gate pulse at a predetermined interval and sends said transfer gate pulse to said CCD area sensor.

3. The endoscope device according to claim 2, said image receiving device further comprising:

an image processor, that processes image data output by said CCD area sensor, wherein said image data output from said CCD area sensor is sent to said image processor each time said transfer gate pulse is generated by said CCD driver.

4. The endoscope device according to claim 3, wherein said control circuit controls said second shutter means, to start transmitting said persistent fluorescence to said image receiving device immediately after said first shutter means stops transmitting said excitation radiation to the organic tissue, a plurality of times during said predetermined interval, and wherein said CCD area sensor accumulates a cumulative voltage, representative of a cumulative intensity of persistent fluorescence over said plurality of times, for each output of image data in response to said transfer gate pulse, and wherein said image processor outputs image data received from said CCD area sensor.

5. The endoscope device according to claim 3, said image processor further comprising a picture memory, and wherein said control circuit controls said second shutter means, to start transmitting said persistent fluorescence to said image receiving device immediately after said first shutter means stops transmitting said excitation radiation to the organic tissue, once during said predetermined interval, and wherein said picture memory accumulates cumulative intensity values, representative of a cumulative intensity of persistent fluorescence over a plurality of transfer gate pulses, and wherein said image processor outputs images formed from said cumulative intensity values.

6. The endoscope device according to claim 1, wherein said first shutter means comprises:

a first shutter located between said light source and said organic tissue, and wherein said second shutter means comprises:

a second shutter between said organic tissue and said image receiving device.

7. The endoscope device according to claim 2, wherein said first shutter means comprises:

a first shutter located between said light source and said organic tissue, and wherein said second shutter means comprises:

an electronic shutter portion of said CCD area sensor controlled by said CCD driver.

8. The endoscope device according to claim 1, wherein said control circuit is further provided with a normal recording mode in which said first shutter means and said second shutter means are controlled so that said image receiving device continuously detects reflected light from said organic tissue.

* * * * *

UNITED STATES PATENT AND TRADEMARK OFFICE
CERTIFICATE OF CORRECTION

PATENT NO. : 5,840,017
DATED : November 24, 1998
INVENTOR(S) : K. FURUSAWA et al.

It is certified that error appears in the above-identified patent and that said Letters Patent is hereby corrected as shown below:

Title Page: item [56], References Cited U.S. Patent Documents, the following items should be changed as indicated:

At reference 4,821,117 "Sekigiguchi" should be ---Sekiguchi---;

At reference 5,295,197 "3/1997" should be ---3/1994---; and "MacCaulay et al" should be ---Macaulay et al---; and
At reference 5,667,474 "9/1997" should be ---3/1995---.

At item [56], add the heading ---Foreign Patent Documents--- and add the following Foreign Documents:
---4-150845 05/25/92 JAPAN---;
---95/26673 10/12/95 WIPO---; and At column 10, line 54 (claim 3, line 3) of the printed patent, "," should be deleted.

Signed and Sealed this

Twenty-eighth Day of March, 2000

Attest:

Q. TODD DICKINSON

*Attesting Officer*  *Commissioner of Patents and Trademarks*

UNITED STATES PATENT AND TRADEMARK OFFICE
CERTIFICATE OF CORRECTION

PATENT NO. : 5,840,017
DATED : November 24, 1998
INVENTOR(S) : K. FURUSAWA et al.

It is certified that error appears in the above-identified patent and that said Letters Patent is hereby corrected as shown below:

On the cover of the printed patent at item [56], References Cited, U.S. Patent Documents, the following item was omitted and should be included:
---5,452,723 09/26/95 WU et al.---

At item [56], add the heading ---Foreign Patent Documents--- and add the following Foreign Documents:
---4-150845 05/25/92 JAPAN---;
---95/26673 10/12/95 WIPO---; and
---0512965 11/12/92 EPO---.

At item [56], add the heading ---Other Publications--- and add the following items:
---Fluorescence Imaging of Early Lung Cancer, by Stephen LAM, et al., published at pages 2-8 of Vol. 2324 of SPIE (6/95)---; and
---Time-Gated Imaging System for Tumor Diagnosis, by Rinaldo CUBEDDU, published at pages 320-325 of Vol.32, No. 2 of February issue of Optical Engineering---.

Signed and Sealed this

Nineteenth Day of September, 2000

Q. TODD DICKINSON

*Attest:*

*Attesting Officer*  *Director of Patents and Trademarks*